US008518659B2

United States Patent
Mori et al.

(10) Patent No.: US 8,518,659 B2
(45) Date of Patent: Aug. 27, 2013

(54) METHOD FOR DETERMINATION OF DEGREE OF RISK OF ONSET OF HIGH-FUNCTIONING AUTISM

(75) Inventors: Norio Mori, Shizuoka (JP); Kazuhiko Nakamura, Shizuoka (JP); Katsuaki Suzuki, Shizuoka (JP); Kenji Tsuchiya, Shizuoka (JP); Keiko Iwata, Shizuoka (JP); Hideo Matsuzaki, Shizuoka (JP)

(73) Assignee: Natonal University Corporation Hamamatsu University School of Medicine, Shizouka (JP)

( * ) Notice: Subject to any disclaimer, the term of this patent is extended or adjusted under 35 U.S.C. 154(b) by 0 days.

(21) Appl. No.: 13/501,147

(22) PCT Filed: Oct. 14, 2010

(86) PCT No.: PCT/JP2010/006114
§ 371 (c)(1),
(2), (4) Date: May 16, 2012

(87) PCT Pub. No.: WO2011/045937
PCT Pub. Date: Apr. 21, 2011

(65) Prior Publication Data
US 2012/0231484 A1    Sep. 13, 2012

(30) Foreign Application Priority Data
Oct. 14, 2009    (JP) .................................. 2009-236976

(51) Int. Cl.
*C12Q 1/60*    (2006.01)
(52) U.S. Cl.
USPC ........................................................ 435/11
(58) Field of Classification Search
None
See application file for complete search history.

(56) References Cited

U.S. PATENT DOCUMENTS

| | | | | |
|---|---|---|---|---|
| 7,223,546 | B2 * | 5/2007 | Miki et al. | 435/7.1 |
| 7,709,213 | B2 * | 5/2010 | Chez | 435/7.1 |
| 2006/0264779 | A1 | 11/2006 | Kemp et al. | |
| 2007/0299096 | A1 * | 12/2007 | Silva | 514/275 |
| 2009/0215097 | A1 * | 8/2009 | Itai et al. | 435/11 |

FOREIGN PATENT DOCUMENTS

| | | |
|---|---|---|
| JP | 2006-180707 A | 7/2006 |
| JP | 2008-032447 A | 2/2008 |
| JP | 2008-141975 A | 6/2008 |
| JP | 2008-544214 A | 12/2008 |
| WO | 2004-087945 A1 | 10/2004 |

OTHER PUBLICATIONS

Foreign search report from PCT/JP2010/006114 Nov. 2010.*
Bagasra O. et al. Role of Perfumes in Pathogenesis of Autism. Medical Hypotheses 80 (2013)795-803.*
Wiest M. et al. Plasma Fatty Acid Profiles in Autism. Prostaglandins, Leukotrienes and Essential Fatty Acids 80(2009)221-227.*
International Search Report for PCT/JP2010/006114; Nov. 16, 2010.
Iwata, Y., et al. "Jiheisho no Massho Seibutsugakuteki Marker no Kensaku". In: Brain 21, vol. 10, No. 3; Jul. 20, 2007; pp. 261-266.
Matsuzaki, H. "A Biomarker for Autism (Jiheisho no Bio Marker)". In: Brain Science and Mental Disorders, vol. 20, No. 4; Dec. 25, 2009; pp. 271-280.
Iwata, K. "Jiheisho no Bunshi Mechanism Kaiseki o Mezashite". In: Bulletin of the Japanese Society for Neurochemistry, vol. 49, No. 1; Mar. 31, 2010; pp. 3-10.
MacIntosh, K.E., et al. "Annotation: The similarities and differences between autistic disorder and Asperger's disorder: a review of the empirical evidence". In: Journal of Child Psychology and Psychiatry vol. 45, No. 3; 2004; pp. 421-434.
McCaffery, P., et al. "Macrocephaly and the control of brain growth in autistic disorders". In: Progress in Neurobiology, vol. 77; 2005; pp. 38-56.
Fatemi, S.H., et al. "Reelin Signaling Is Impaired in Autism". In: Biol Psychiatry, vol. 57; 2005; pp. 777-787.
Corbett, B.A., et al. "A proteomic study of serum from children with autism showing differential expression of apolipoproteins and complement proteins". In: Molecular Psychiatry; Vo. 12; 2007; pp. 292-306.
Kim, E-Y., et al. "Alterations in lipid profile of autistic boys: a case control study". In: Nutrition Research, vol. 30; 2010; pp. 255-260.
Dziobek, I., et al. "Hypercholesterolemia in Asperger syndrome: Independence from lifestyle, obsessive-compulsive behavior, and social anxiety". In: Psychiatry Research, vol. 149; 2007; pp. 321-324.
Tierney, E., et al. "Abnormalities of Cholesterol Metabolism in Autism Spectrum". In: Am J Med Genet B Neuropsychiatr Genet, vol. 141B(6); Sep. 5, 2006; pp. 666-668.
Bukelis, I., et al. "Smith-Lemli-Optiz Syndrome and Autism Spectrum Disorder". Clinical Case Conference from the Johns Hopkins University School of Medicine. In: Am J Psychiatry, vol. 164; Nov. 11, 2007; pp. 1655-1661.

* cited by examiner

*Primary Examiner* — Ralph Gitomer
(74) *Attorney, Agent, or Firm* — Pearne & Gordon LLP

(57) ABSTRACT

The present invention relates to a method for determining the degree of risk of onset of autism, comprising the step of measuring the triglyceride concentration or the cholesterol concentration in a very low-density lipoprotein fraction of plasma or serum isolated from a subject, or the triglyceride concentration or the cholesterol concentration of plasma or serum. In addition, the present invention provides a kit for determining the degree of risk of onset of autism and a method for screening for a candidate substance for agents for treating autism using a non-human mammal, in which the above described method is utilized.

4 Claims, 3 Drawing Sheets

METHOD FOR DETERMINATION OF DEGREE OF RISK OF ONSET OF HIGH-FUNCTIONING AUTISM

This application is a National stage application filed under Rule 371 based on PCT/JP2010/006114 filed Oct. 14, 2010.

TECHNICAL FIELD

The present application claims priority from Japanese Patent Application No. 2009-236976 (filed on Oct. 14, 2009); the disclosure of which is hereby incorporated by reference.

The present invention relates to a method for discovering an autistic patient at an early stage. More specifically, the present invention relates to a method for determining the degree of risk of onset of autism, comprising the step of measuring a very low-density lipoprotein contained in plasma or serum isolated from a subject. Moreover, it relates to a method for determining the degree of risk of onset of autism, comprising the step of measuring the cholesterol concentration and/or the triglyceride concentration in plasma or serum.

BACKGROUND ART

Autism is a disorder that has been first identified as "autistic disturbances of affective contact" by Dr. Kanner in U.S.A. in 1943. Onset of autism appears in an extremely early stage (before turning about three years old), and it includes, as principal symptoms, severe and sustained impairment in social interaction, deviance in communication, and patterns of behavior and interest that are restricted or stereotyped. Autism is a developmental disorder in which the condition changes in the course of development, and it is assumed to be a yet unspecified high-level central nervous system disorder.

High-functioning autism means autism, which does not have mental retardation. With regard to autism morbidity, it has been reported that 7 to 16 out of 10,000 children suffer from autism, and that high-functioning autism is about 11% to 34% of the autism (Macintosh et al., Journal of Child Psychology and Psychiatry 2004).

The cause of autism has not been clarified at present, and thus, the radical treatment method for autism has not been developed yet. Accordingly, educational intervention by experts (which is referred to as "intensive intervention") based on early detection is important for the adaptation to social life of autistic patients. The earlier the time of initiation of such intensive intervention, the more effective it becomes. It is desired to begin such intervention before or after a child is two years old, at which the autistic symptoms appear for the first time. However, since objective and biological criteria for autism have not been established yet, doctor must diagnose autism only based on symptoms. For such diagnosis, abundant experience at the site of child psychiatry is required. Thus, under the circumstances in which there is a shortage of experts in this field, it is extremely difficult to detect an autistic patient at an early stage.

At present, the diagnosis of autism is made by conducting an interview with subjects using the diagnostic criteria of the American Psychiatric Association (DSM-IV), ICD-10 of World Health Organization (WHO), and ADI-R (Autism Diagnostic Interview-Revised).

Although the cause of autism has not been clarified yet, various reports have been made so far. For example, enlarged head circumference is observed at an early stage after the birth of an autistic child, and thus, it is considered that an increase in neurogenesis and/or gliogenesis or a decrease in cell death during this period is associated with the development of autism (McCaffery et al., Progress in Neurobiology 2005). Other than this report, Fatemi et al. have focused on developmental disorders of the central nerve system found in Reeler mice, and have reported that an increase in the mRNA level of a very low-density lipoprotein receptor (VLDL receptor) that is a receptor of the responsible gene Reelin of the Reeler mouse is found in the frontal lobe and cerebellum of an autistic patient after death (Fatemi et al., 2005). On the other hand, Sharp et al. have made a proteome analysis, and as a result, they have found a decrease in the concentration of apolipoprotein B-100 specific to autistic children (Corbett et al., 2007). Basically, VLDL is a complex of protein and lipid containing the apolipoprotein B-100, and a change in the expression of this molecule in vivo is anticipated to be associated with lipid metabolism. However, to date, there have been no reports of the lipid fractions of peripheral blood of autistic patients. Also, there have been no reports stating the relationship between autistic patients and serum lipid levels.

In addition, there has been disclosed an invention relating to the diagnosis of autism by measuring the amounts of specific growth factors in a serum sample (Japanese Patent Laid-Open No. 2008-32447). However, the behavior of these growth factors is never associated with lipid metabolism.

As described above, taking into consideration the specificity of the pathologic condition of autism, studies have been conducted directed towards establishing a comprehensive treatment system including prevention of this disorder based on early diagnosis, early treatment, and support of patients for social rehabilitation. However, a biological marker for autism, which enables early diagnosis, has not been developed yet.

CITATION LIST

Patent Literature

[Patent Literature 1] Japanese Patent Laid-Open No. 2008-32447

[Non Patent Literature]

[Non Patent Literature 1] Macintosh et al., Journal of Child Phychology and Psychiatry 2004
[Non Patent Literature 2] McCaffery et al., Progress in Neurobiology 2005
[Non Patent Literature 3] Fatemi et al., 2005
[Non Patent Literature 4] Corbett et al., 2007

SUMMARY OF INVENTION

Technical Problem

It is an object of the present invention to provide an objective and simple method for determining the degree of risk of onset of autism, using a biological marker, and to enable to provide an appropriate treatment to the autistic patient at an early stage by finding an autistic patient at an early stage using the aforementioned method.

Solution to Problem

In order to achieve the aforementioned object, the present inventors have collected serum samples from a high-functioning autism group and a healthy control group and have made a comparison between them. As a result, the inventors have found that the triglyceride concentrations in the very low-density lipoprotein fractions of underage autistic patients are significantly decreased, and based on such a phenomenon, they have completed the present invention.

Moreover, the present inventors have collected serum samples from a high-functioning autism group and a healthy control group and have made a comparison between them. As a result, the inventors have found that the total amounts of cholesterol and triglyceride are significantly decreased in underage autistic patients, and that the cholesterol concentrations in the very low-density lipoprotein fractions of underage autistic patients are significantly decreased. The inventors have completed the present invention based on these phenomena.

Specifically, the present invention relates to a method for determining the degree of risk of onset of autism, comprising the step of measuring a very low-density lipoprotein contained in plasma or serum isolated from a subject, wherein the degree of risk of onset of autism of the subject is determined to be high when the triglyceride concentration in a very low-density lipoprotein fraction of the plasma or serum is 60 mg/dl or less.

The above described subject is desirably 18 years old or younger.

In addition, when the above described subject is 8 years old or younger and the triglyceride concentration in the very low-density lipoprotein fraction of the serum is 30 mg/dl or less, the degree of risk of onset of autism of the subject is determined to be high.

Moreover, the present invention provides a kit for determining the degree of risk of onset of autism, comprising one or more enzymes selected from the group consisting of lipoprotein lipase, glycerol kinase, glycerol-3-phosphate oxidase, peroxidase, ascorbate oxidase, pyruvate kinase, and lactate dehydrogenase; and a coloring agent.

Furthermore, the present invention provides a method for screening for a candidate substance for agents for treating autism, comprising the steps of:
(a) administering a test substance to a non-human mammal;
(b) isolating plasma or serum from the non-human mammal;
(c) measuring the triglyceride concentration in a very low-density lipoprotein fraction of the isolated plasma or serum; and
(d) determining that the test substance is a candidate substance for agents for treating autism, if indicated by the triglyceride concentration in the very low-density lipoprotein fraction of the plasma or serum being increased, as compared with that before the administration of the test substance.

Further, the present invention provides a method for determining the degree of risk of onset of autism, comprising the step of measuring a very low-density lipoprotein contained in plasma or serum isolated from a subject, wherein the degree of risk of onset of autism of the subject is determined to be high when the cholesterol concentration in a very low-density lipoprotein fraction of the plasma or serum is lower than a standard value minus standard deviation of the cholesterol concentrations in a very low-density lipoprotein fractions of the plasma or serum of healthy individuals.

Still further, the present invention provides a method for determining the degree of risk of onset of autism, comprising the step of measuring the cholesterol concentration and/or the triglyceride concentration in plasma or serum isolated from a subject, wherein the degree of risk of onset of autism of the subject is determined to be high when the measured concentration of cholesterol is lower than a standard value minus standard deviation of the cholesterol concentrations in healthy individuals, and/or when the measured concentration of triglyceride is lower than a standard value minus standard deviation of the triglyceride concentrations in healthy individuals.

Still further, the present invention provides a kit for determining the degree of risk of onset of autism, comprising cholesterol oxidase, peroxidase, and a coloring agent.

The above described autism may be high-functioning autism.

Advantageous Effects of Invention

According to the present invention, biological criteria for determining the degree of risk of onset of high-functioning autism have been determined for the first time. In addition, the present invention can be carried out by a method involving collection of peripheral blood, which is simple and which is able to reduce burden to subjects to the minimum.

According to the present invention, the diagnosis of autism, which has mainly been made by a doctor's subjective view so far, can be made by a comprehensive diagnosis attended with biological criteria. Thus, the improvement of a diagnostic technique can be anticipated. The earlier the intensive intervention that is given to autistic patients, the more effective it would be. Since the method of the present invention can be applied to infants and children, it enables early finding of autism and initiation of intensive intervention to autistic children at an early stage. This is extremely effective for autistic children who will organize their social life in the future. Moreover, nowadays, troubles caused by autistic patients have gained prominent attention. From the viewpoint of coping with these problems, the present invention has great social effects.

The present invention enables simple and reliable diagnosis of autism at an early stage. In particular, by measuring a triglyceride concentration in a VLDL fraction of a human blood sample at two stages, the diagnosis of autism can be easily assisted.

DESCRIPTION OF EMBODIMENTS

Figure 1:
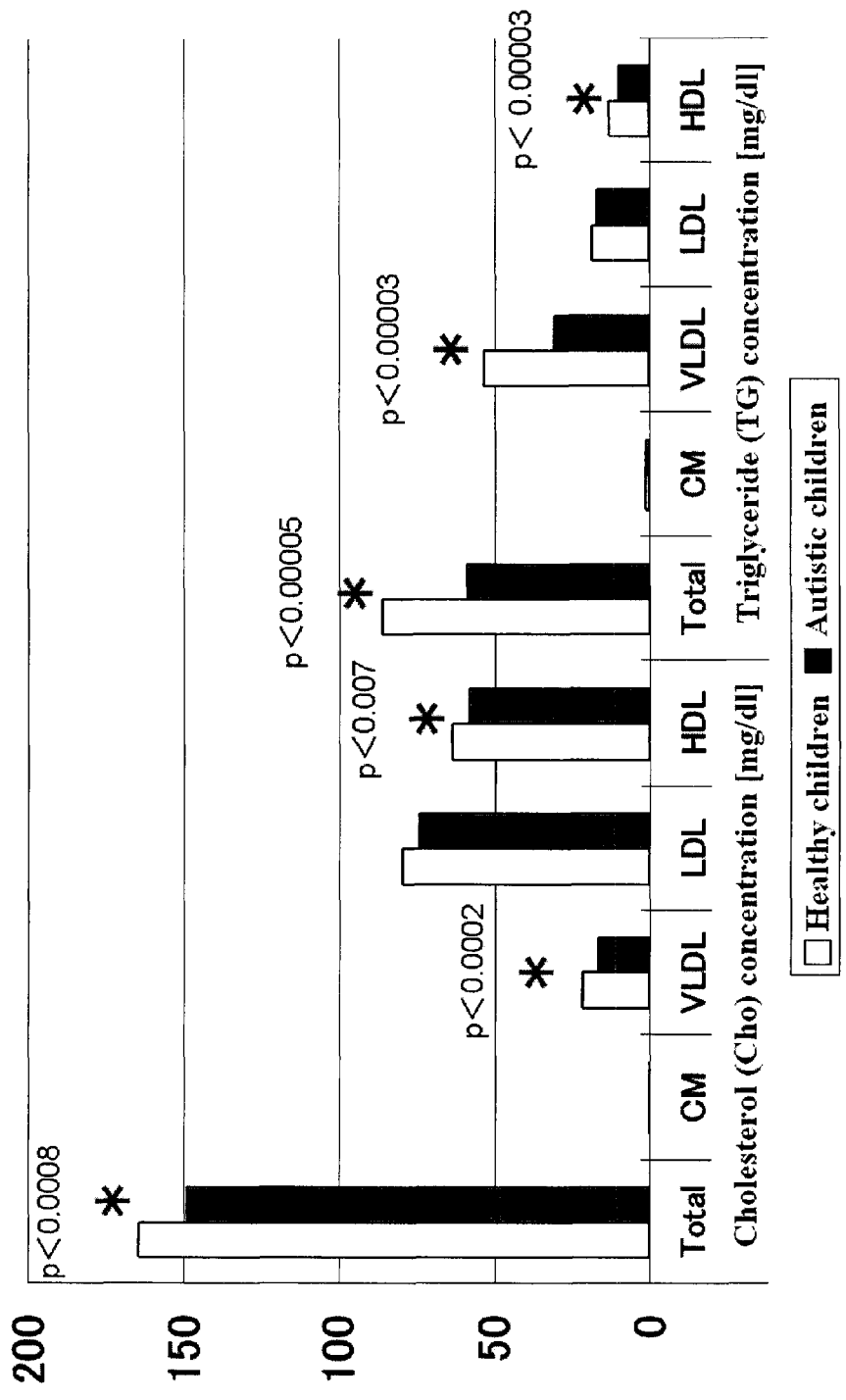
FIG. 1 shows the mean values of lipoprotein fraction concentrations in a serum lipid in an underage high-functioning autistic patient group and an underage healthy control group.

The present invention relates to a method for detecting an autistic patient at an early stage. More specifically, the present invention relates to a method for determining the degree of risk of onset of autism, comprising the step of measuring a very low-density lipoprotein contained in serum isolated from a subject.

1. Definition

"Autism" is one of pervasive developmental disorders, which is diagnosed during childhood. Main symptoms, such as communication disorder, impaired social interaction, restricted interest and behavior, hyperaesthesia, and hyperactive tendency, appear before an autistic patient turns 3 years old. "High-functioning autism" means the above described autism, which does not have mental retardation.

In the invention of the present application, the "degree of risk of onset of autism" means a criterion for determination of autism, which is used for determining whether or not a subject will develop autism, or whether or not a subject has developed autism. The higher the degree of risk of onset of autism, the more likely the subject will develop autism, or the subject is diagnosed to be an autistic patient. In contrast, the lower the degree of risk of onset of autism, the more unlikely the subject will develop autism, or it is determined that the subject is healthy.

"Very low-density lipoprotein (VLDL)" is one type of lipoprotein present in blood. Such lipoproteins are classified depending on the density measured by centrifugation. The lipoprotein includes a chylomicron (CM), an intermediate-density lipoprotein (IDL), a low-density lipoprotein (LDL) and a high-density lipoprotein (HDL), as well as VLDL. These lipoproteins share the property that they are composed of protein, triglyceride, free cholesterol, cholesterol ester, and phospholipid. However, they are different from one another in that each lipoprotein comprises a characteristic apoprotein and has a different lipid composition.

A "very low-density lipoprotein fraction" or "VLDL fraction" means a fraction having a density of 0.950 to 1.006 g/ml, which is obtained by centrifugation of plasma or serum. Likewise, a "chylomicron fraction" or "CM fraction" means a fraction having a density of <0.95 g/ml, which is obtained by centrifugation of plasma or serum. A "low-density lipoprotein fraction" or "LDL fraction" means a fraction having a density of 1.019 to 1.063 g/ml, which is obtained by centrifugation of plasma or serum. A "high-density lipoprotein fraction" or "HDL fraction" means a fraction having a density of 1.063 to 1.210 g/ml, which is obtained by centrifugation of plasma or serum.

"Triglyceride," "triacylglycerol," or "TG" means a triester compound of fatty acid and glycerol.

The term "underage" or "child" is used in the present invention to mean a human who is 18 years old or younger.

The term "cutoff value" is used herein to mean a value used to distinguish a target disease group from a non-disease group, when focusing on a certain substance. When such a target disease group is distinguished from a non-disease group, if the value is smaller than the cutoff value, it can be determined to be negative, and if the value is greater than the cutoff value, it can be determined to be positive. On the other hand, if the value is smaller than the cutoff value, it can be determined to be positive, and if the value is greater than the cutoff value, it can be determined to be negative, thereby determining the development of the disease.

Indicators used for the purpose of evaluating the clinical usefulness of a cutoff value include sensitivity and specificity.

A certain population is determined using a cutoff value. Among suspected patients of a certain disease, patients who are determined to be positive are defined as "a" (true positive), patients who are determined to be negative although they are affected with the certain disease are defined as "b" (false-negative), patients who are determined to be positive although they are not affected with the certain disease are defined as "c" (false-positive), and patients who are determined to be negative and they are not affected with the certain disease are defined as "d" (true negative). The value represented by a/(a+b) indicates sensitivity (true positive rate), and the value represented by d/(c+d) indicates specificity (true negative rate).

With regard to distribution of the measurement values of a target disease group and a non-disease group, the distribution is generally overlapped. Accordingly, sensitivity and specificity are changed by increasing or decreasing a cutoff value. When the cutoff value is decreased, sensitivity is increased, but specificity is decreased. In contrast, when the cutoff value is increased, sensitivity is decreased, but specificity is increased. For a determination method, both the values of sensitivity and specificity are preferably high. In addition, a determination method, in which the values of sensitivity and specificity do not exceed 0.5, is not considered to be useful.

2. Method for Determining the Degree of Risk of Onset of Autism

The present invention relates to a method for determining the degree of risk of onset of autism, comprising the step of measuring a very low-density lipoprotein contained in plasma or serum isolated from a subject.

(1) Isolation Step

As a sample to be measured in the present invention, in general, plasma or serum is prepared from blood collected from a subject, and is then used. In the present invention, peripheral blood can be used as a sample. As a method of preparing plasma or serum, a method well known in the art can be used. The prepared plasma or serum may be frozen for preservation before subjecting to measurement.

(2) Measurement Step

In the present invention, a measurement step is carried out by separating plasma or serum isolated from a subject to obtain fractions according to a method well known in the art, such as an ultracentrifugal method or gel filtration, and then measuring the triglyceride concentration or cholesterol concentration in each fraction. If a gel filtration HPLC method is applied, serum can be separated, and each fraction can be then detected and quantified. There is no difference in the lipid concentration between in plasma and in serum.

As described above, depending on density, lipoproteins contained in plasma or serum are divided into a chylomicron, IDL, VLDL, LDL, and HDL. Separation of serum into individual fractions and the subsequent quantification can be carried out according to a well known method such as a gel filtration HPLC method.

(i) Measurement of Triglyceride Concentration

In the present invention, the triglyceride concentration in VLDL may be directly measured, and the degree of risk of onset of autism may be then determined based thereon. Alternatively, a two-stage measurement may be carried out. Specifically, the total amount of triglyceride contained in plasma or serum may be first measured. Then, when the total amount of triglyceride is less than a predetermined value, the triglyceride concentration in a VLDL fraction may be measured, and the degree of risk of onset of autism may be then determined. In the case of carrying out such a two-stage measurement, it is preferable that the triglyceride concentration in a VLDL fraction be measured to determine the degree of risk of onset of autism, when the total amount of triglyceride is less than 80 mg/dl, preferably less than 70 mg/dl, and more preferably less than 60 mg/dl. By performing the measurement at two stages, the diagnosis of autism can be easily assisted.

The concentration of triglyceride can be determined by measuring it by a glycerol kinase (GK)-glycerol-3-phosphate oxidase (GPO) method, a glycerol oxidase (GOD) method, a glycerol dehydrogenase (GDH) method, etc., based on a method of measuring glycerin produced from triglyceride with the use of lipoprotein lipase (LPL).

For instance, in the case of a GPO-DAOS method, the amount of triglyceride can be measured by quantifying hydrogen peroxide produced with the use of lipoprotein lipase (LPL), glycerol kinase (GK), glycerol-3-phosphate oxidase (GPO) and peroxidase (POD), using DAOS. Specifically, the GPO-DAOS method comprises the following steps:

1) degrading triglyceride contained in a sample into glycerin and fatty acid by the action of lipoprotein lipase (LPL);
2) converting the produced glycerin to glycerol-3-phosphate by the action of glycerol kinase (GK) in the presence of ATP;
3) oxidizing the produced glycerol-3-phosphate by the action of glycerol-3-phosphate oxidase (GPO), and at the same time, producing hydrogen peroxide;
4) allowing the produced hydrogen peroxide to cause quantitative oxidative condensation of N-methyl-N-(2-hydroxy-3-sulfopropyl)-3,5-dimethoxyaniline sodium salt (DAOS) and 4-aminoantipyrine by the action of peroxidase (POD), so as to produce a blue dye; and
5) measuring the absorbance of the produced blue dye, thereby calculating the triglyceride concentration in the sample.

Likewise, in the case of a "NAD" method, the produced hydrogen peroxide is quantified using lipoprotein lipase (LPL), glycerol kinase (GK), pyruvate kinase, and lactate dehydrogenase.

(ii) Measurement of Cholesterol Concentration

In the present invention, the cholesterol concentration in VLDL may be directly measured, and the degree of risk of onset of autism may be then determined based thereon. Alternatively, a two-stage measurement may be carried out. Specifically, the total amount of cholesterol contained in plasma or serum may be first measured. Then, when the total amount of cholesterol is less than a predetermined value, the cholesterol concentration in a VLDL fraction may be measured, and the degree of risk of onset of autism may be then determined. By performing the measurement at two stages, the diagnosis of autism can be easily assisted.

The concentration of cholesterol can be determined by measuring it by a cholesterol oxidase-DAOS method or the like.

For instance, in the case of the cholesterol oxidase-DAOS method, the amount of cholesterol can be measured by quantifying hydrogen peroxide produced with the use of cholesterol oxidase, using DAOS. Specifically, the cholesterol oxidase-DAOS method comprises the following steps:
1) oxidizing cholesterol contained in a sample by the action of cholesterol oxidase, so as to produce a ketone body and hydrogen peroxide;
2) allowing the produced hydrogen peroxide to cause quantitative oxidative condensation of N-ethyl-N-(2-hydroxy-3-sulfopropyl)-3,5-dimethoxyaniline sodium salt (DAOS) and 4-aminoantipyrine by the action of peroxidase, so as to produce a blue dye; and
3) measuring the absorbance of the produced blue dye, thereby calculating the cholesterol concentration in the sample.

In another aspect of the present invention, the measurement step is carried out by measuring the total amount of triglyceride or the total amount of cholesterol contained in plasma or serum isolated from a subject.

(3) Determination Step

The present inventors have found that the triglyceride concentration in a VLDL fraction is almost constant in healthy individuals regardless of their age, but that, in the case of autistic patients, the triglyceride concentration in a VLDL fraction is low in their childhood and then increases with aging.

Based on this finding, in the present invention, when the triglyceride concentration in the VLDL fraction of a subject, which is measured by the above described method, is lower than a standard value minus standard deviation of the triglyceride concentrations in the VLDL fractions of healthy individuals, the degree of risk of onset of autism of the subject is determined to be high. Specifically, when the triglyceride concentration in the VLDL fraction of a subject is 60 mg/dl or less, and preferably 50 mg/dl or less, the degree of risk of onset of autism of the subject is determined to be high. Preferably, when the triglyceride concentration in the VLDL fraction of a subject who is 18 years old or younger is 50 mg/dl or less and preferably 40 mg/dl or less, the degree of risk of onset of autism of the subject is determined to be high. More preferably, when the triglyceride concentration in the VLDL fraction of a subject who is 8 years old or younger is 40 mg/dl or less and preferably 30 mg/dl or less, the degree of risk of onset of autism of the subject is determined to be high.

Moreover, the present inventors have found that the cholesterol concentration in the very low-density lipoprotein fraction of an autistic patient is significantly decreased, when compared with those of healthy individuals. Based on this finding, in the present invention, when the cholesterol concentration in the VLDL fraction of a subject, which is measured by the above described method, is lower than a standard value minus standard deviation of the cholesterol concentrations in the VLDL fractions of healthy individuals, the degree of risk of onset of autism of the subject is determined to be high. Specifically, when the cholesterol concentration in the VLDL fraction of a subject is 20 mg/dl or less, and preferably 15 mg/dl or less, the degree of risk of onset of autism of the subject is determined to be high.

Furthermore, the present inventors have found that the total amounts of cholesterol and triglyceride of autistic patients are significantly decreased, when compared with those of healthy individuals. Based on this finding, in the present invention, when the triglyceride concentration or cholesterol concentration of the plasma or serum of a subject, which is measured by the above described method, is lower than a standard value minus standard deviation of the triglyceride concentrations or cholesterol concentrations of healthy individuals, the degree of risk of onset of autism of the subject is determined to be high. Specifically, when the cholesterol concentration is 160 mg/dl or less and preferably 150 mg/dl or less, or when the triglyceride concentration is 80 mg/dl or less and preferably 60 mg/dl or less, the degree of risk of onset of autism of the subject is determined to be high.

According to the present invention, the degree of risk of onset of high-functioning autism can be determined by a simple method using peripheral blood, at a high proper diagnosis rate in an early stage.

3. Kit for Determining the Degree of Risk of Onset of Autism

The kit according to the present invention may be a kit for carrying out the method for determining the degree of risk of onset of autism, described in the above section 2. Specific constitution, materials, devices and the like included in the kit are not particularly limited.

For example, the kit of the present invention comprises, but not limited to, reagents for measuring the triglyceride in isolated peripheral blood plasma or peripheral blood serum, or in the VLDL of peripheral blood: one or more enzymes which are selected from lipoprotein lipase (LPL), glycerol kinase (GK), glycerol-3-phosphate oxidase (GPO), glycerol oxidase (GOD), glycerol dehydrogenase (GDH), pyruvate kinase, lactate dehydrogenase, peroxidase, and the like, and a coloring agent such as DAOS or FDAOS. The present kit may further comprise a buffer necessary for the measurement.

In the case of measuring the triglyceride concentration according to the GPO-DAOS method for example, the kit of the present invention may comprise one or more selected from glycerin, a buffer (PIPES; pH 6.5), lipoprotein lipase, adenosine-5'-phosphate disodium trihydrate (ATP), glycerol kinase, glycerol-3-phosphate oxidase (GPO), peroxidase, N-ethyl-N-(2'-hydroxy-3'-sulfopropyl)-3,5-dimethoxyaniline sodium (DAOS), 4-aminoantipyrine and ascorbate oxidase.

Further, the kit of the present invention may comprise, but not limited to, reagents for measuring the cholesterol in isolated peripheral blood plasma or peripheral blood serum, or in the VLDL of peripheral blood, such as cholesterol oxidase, peroxidase, and a coloring reagent.

Using the above described kit, the degree of risk of onset of high-functioning autism can be determined.

Still further, the kit for determining the degree of risk of onset of autism according to the present invention can also be used as a kit for the after-mentioned method for screening for a candidate substance for agents for treating autism.

4. Method for Screening for Candidate Substance for Agents for Treating Autism The determination method or determination kit of the present invention can be applied to a method for screening for a candidate substance for agents for treating autism using a non-human mammal. As such a non-human mammal, mammals other than humans may be used. Examples of such a non-human mammal include a mouse, rat, and monkey.

The present invention provides a method for screening for a candidate substance for agents for treating autism, comprising the steps of:

(a) administering a test substance to a non-human mammal;
(b) isolating plasma or serum from the non-human mammal;
(c) measuring the triglyceride concentration in a very low-density lipoprotein fraction of the isolated plasma or serum; and
(d) determining that the test substance is a candidate substance for agents for treating autism, if indicated by the triglyceride concentration in the very low-density lipoprotein fraction of the plasma or serum being increased, as compared with that before the administration of the test substance.

In another aspect of the present invention, increases in the triglyceride concentration or cholesterol concentration in peripheral blood plasma or peripheral blood serum, or the cholesterol concentration in a very low-density lipoprotein fraction of peripheral blood plasma or peripheral blood serum can be used as an indicator for screening for a candidate substance for agents for treating autism.

Using this screening method, a candidate substance for agents for treating high-functioning autism can be selected.

Hereinafter, the present invention will be described more in detail in the following examples. However, these examples are not intended to limit the scope of the present invention.

EXAMPLES

1. Subject

As subjects, 106 male patients with high-functioning autism [average age: 14.7 years old (standard deviation: 5.9); age range: 6 to 30 years old] were selected. At the same time, 112 healthy individuals in the same age range [average age: 15.1 years old (standard deviation: 6.2); age range: 6 to 30 years old] were selected as healthy controls. All patients were diagnosed in accordance with diagnostic criteria for high-functioning autism, ADI-R (Autism Diagnostic Interview-Revised).

2. Experimental Method

A serum specimen was collected from each subject, and it was then preserved at −80° C. before subjecting to measurement. The cholesterol and triglyceride in a lipid fraction were subjected to a measurement comparison according to a HPLC method. The triglyceride concentration in a VLDL fraction was measured according to a gel filtration HPLC method, and this measurement was performed by Skylight-Biotech on a commission basis.

3. Statistical Analysis

Data were shown using mean values. Statistical analysis between the two groups was carried out by a t-test. A p-value of less than 0.01 was defined to be statistically significant.

4. Results (1) Decrease in Serum Lipid Concentration in Autistic Patients

The mean values of serum lipid concentrations in lipoprotein fractions, in underage healthy controls and underage subjects with high-functioning autism, are shown in Table 1 and FIG. 1.

TABLE 1

| | Cholesterol (Cho) concentration [mg/dl] | | | | | Triglyceride (TG) concentration [mg/dl] | | | | |
|---|---|---|---|---|---|---|---|---|---|---|
| | Total | CM | VLDL | LDL | HDL | Total | CM | VLDL | LDL | HDL |
| Healthy children | 164.7637 | 0.123333 | 21.50227 | 79.75493 | 63.38373 | 86.21187 | 1.188667 | 53.57893 | 18.48773 | 12.95613 |
| Autistic children | 148.8515 | 0.120972 | 16.58139 | 74.10264 | 58.04569 | 58.72208 | 1.288889 | 30.62264 | 16.93903 | 9.872917 |
| p-value | 0.000763 | 0.854019 | 0.000166 | 0.119219 | 0.00678 | 4.17E-05 | 0.85368 | 2.18E-05 | 0.032066 | 2.63E-05 |

As is apparent from FIG. 1, it was found that, with regard to the serum lipids of the underage subjects with high-functioning autism, the total amounts of both cholesterol and triglyceride were significantly decreased, as compared with the underage healthy controls. Moreover, as a result of the measurement of the cholesterol and triglyceride concentrations in each lipoprotein fraction, chylomicron, VLDL, LDL and HDL, it was also found that both the cholesterol and triglyceride concentrations were decreased in the VLDL fraction and the HDL fraction, and that the concentrations were particularly significantly decreased in the VLDL fraction. There was found no significant difference in the chylomicron fraction and the LDL fraction.

Figure 2:
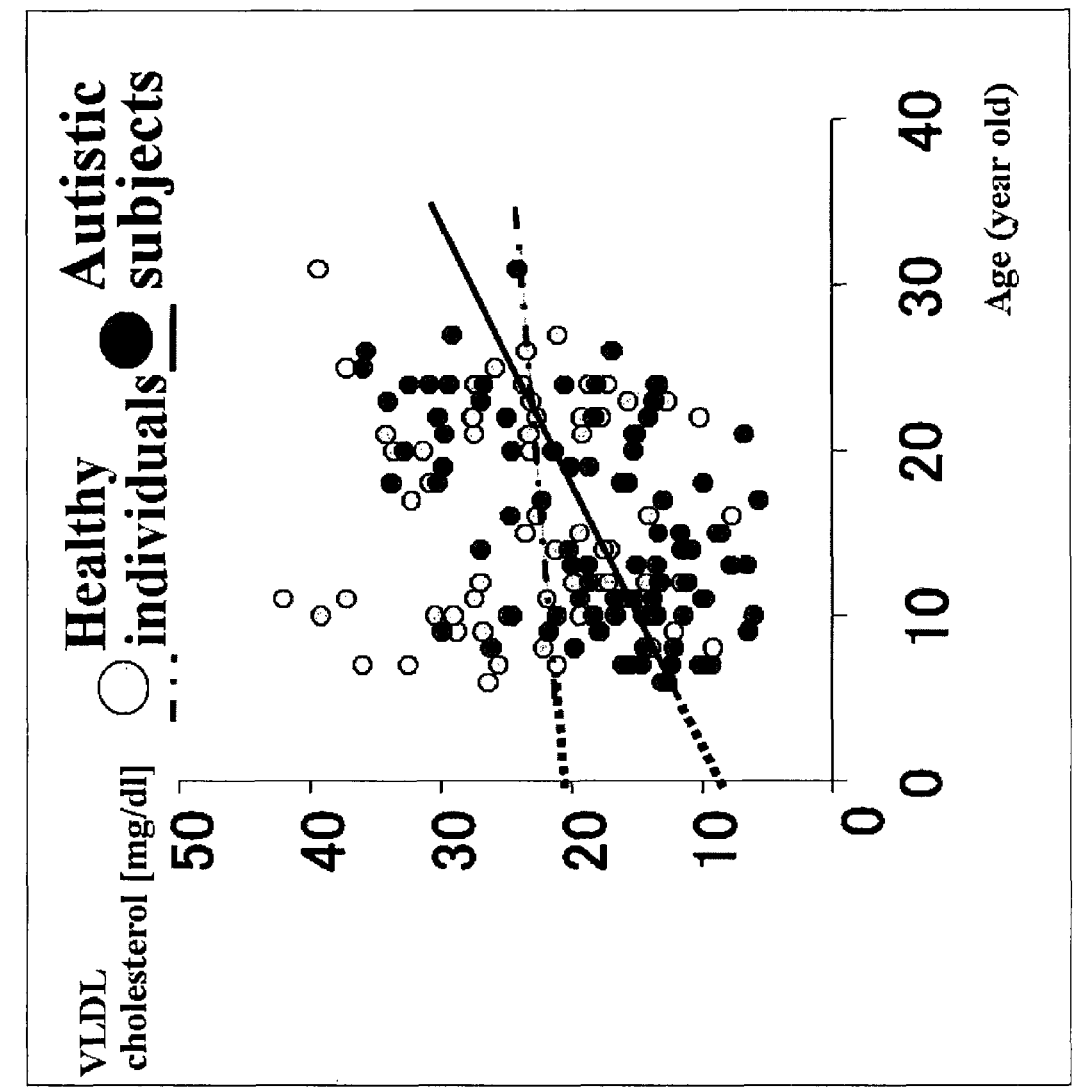
FIG. 2 shows the relationship between the cholesterol concentration in a VLDL fraction and age, in autistic patients and healthy control subjects.

(2) Correlation Between Decrease in Cholesterol Concentration/Triglyceride Concentration in VLDL Fraction and Age The relationship between the cholesterol concentration in a VLDL fraction and age, in autistic patients and healthy controls, is shown in FIG. 2. The relationship between the triglyceride concentration in a VLDL fraction and age, in autistic patients and healthy controls, is shown in FIG. 3.

As is apparent from FIG. 2, the cholesterol concentrations in the VLDL fractions of healthy controls are constant regardless of age. On the other hand, the cholesterol concentrations in the VLDL fraction of autistic patients are the lowest in the childhood, and then they increase with aging.

Figure 3:
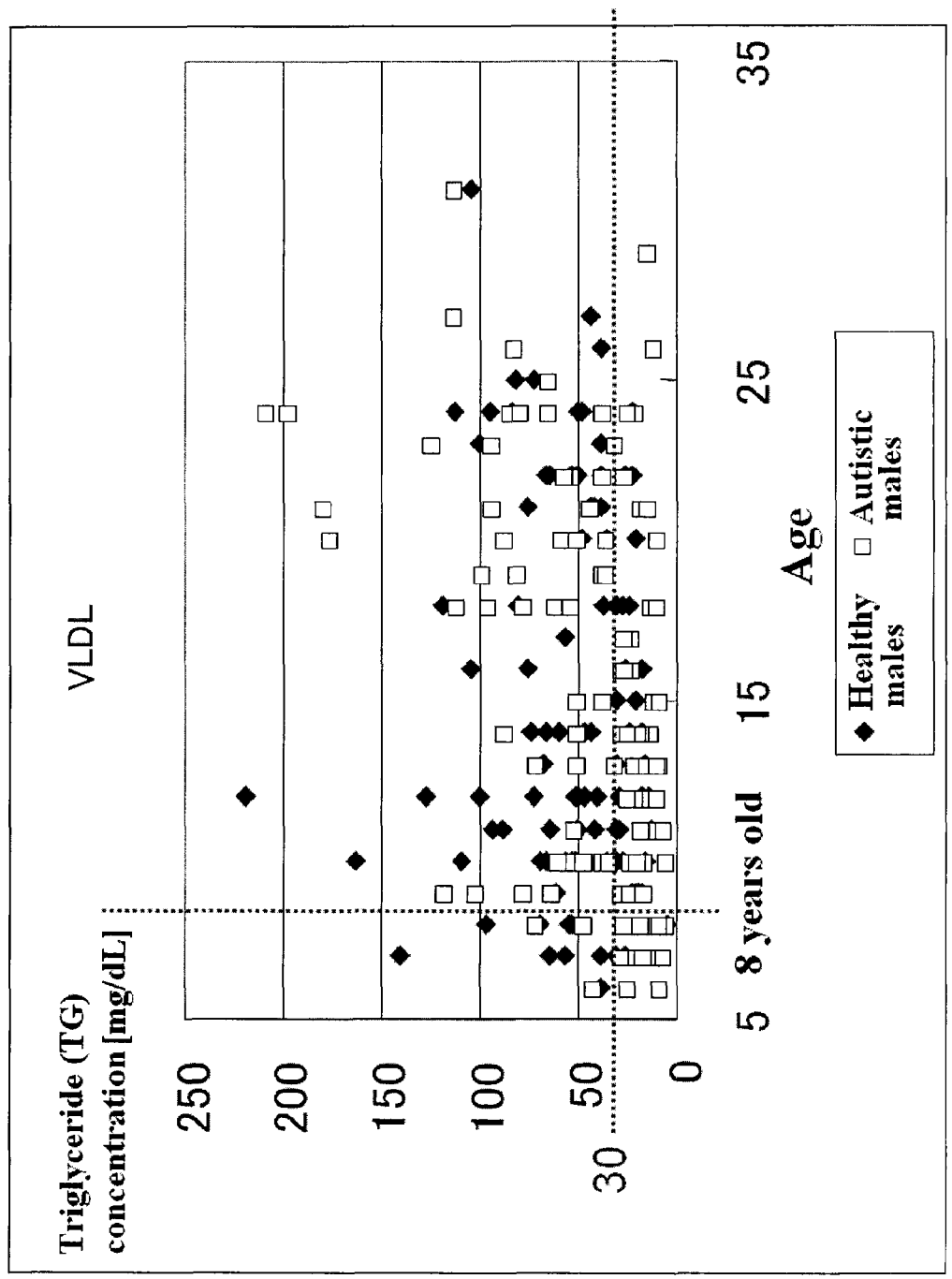
FIG. 3 shows the relationship between the triglyceride concentration in a VLDL fraction and age, in autistic patients and healthy control subjects, and a cutoff value used to determine high-functioning autistic patients.

Since triglyceride is a major lipid contained in VLDL, the aforementioned tendency was much clearly observed in the case of triglyceride concentration (FIG. 3). Accordingly, a decrease in the triglyceride concentration in a VLDL fraction was considered to be effective for early diagnosis of high-functioning autism.

(3) Cutoff Value

The tendency that the concentrations in the VLDL fractions of autistic patients are low in the childhood of autistic patients and then increase with aging was more clearly observed in the case of the triglyceride concentration than in the case of the cholesterol concentration. Thus, the cutoff value of the triglyceride concentration was investigated.

As a result, when the triglyceride concentration in the VLDL fraction of patients who were 8 years old or younger was lower than 30 mg/dl, patients with high-functioning autism could be selected at high rates (sensitivity: 83%; specificity: 90%; proper diagnosis rate: 86%) (FIG. 3). It is to be noted that sensitivity was 63%, specificity was 72%, and proper diagnosis rate was 67% in the case of all of underage patients, namely, patients who were 18 years old or younger.

Therefore, as a result of the present experiment, it could be confirmed that the triglyceride concentration in a VLDL fraction of blood is useful as a biological marker for autism.

[Industrial Applicability]

According to the present invention, the diagnosis of autism, which has mainly been made by a doctor's subjective view so far, can be carried out by introduction of biological criteria. Accordingly, the improvement of a diagnostic technique can be anticipated. In addition, the earlier the time of initiation of intensive intervention given to autistic patients, the more effective that can be anticipated. The method of the present invention can be applied to infants or children, and thus, it enables the establishment of a comprehensive treatment system including prevention of this disease, early treatment, and support of patients for social rehabilitation, based on early diagnosis.

The invention claimed is:

1. A method for determining the degree of risk of onset of autism, comprising the step of measuring a very low-density lipoprotein contained in plasma or serum isolated from a subject, wherein the degree of risk of onset of autism of the subject is determined to be high when the triglyceride concentration in a very low-density lipoprotein fraction of the plasma or serum is 60 mg/dl or less.

2. The method for determining the degree of risk of onset of autism according to claim 1, wherein the degree of risk of onset of autism of the subject is determined to be high when the triglyceride concentration in a very low-density lipoprotein fraction of the plasma or serum from a subject who is 18 years old or younger is 60 mg/dl or less.

3. The method for determining the degree of risk of onset of autism according to claim 1, wherein the degree of risk of onset of autism of the subject is determined to be high when the triglyceride concentration in a very low-density lipoprotein fraction of the plasma or serum from a subject who is 8 years old or younger is 30 mg/dl or less.

4. The method according to claim 1 wherein the autism is high-functioning autism.

* * * * *